United States Patent [19]

Dennis

[11] 4,020,346
[45] Apr. 26, 1977

[54] X-RAY INSPECTION DEVICE AND METHOD

[76] Inventor: Donald A. Dennis, 80 Seaview, Chatham, Mass. 02633

[22] Filed: Feb. 19, 1975

[21] Appl. No.: 550,993

Related U.S. Application Data

[63] Continuation-in-part of Ser. No. 343,566, March 21, 1973, abandoned.

[52] U.S. Cl. .......................... 250/358 R; 250/453; 250/519
[51] Int. Cl.² ..................................... G01N 23/00
[58] Field of Search .......... 250/358, 359, 360, 312, 250/416 TV, 453, 519

[56] References Cited

UNITED STATES PATENTS

| | | | |
|---|---|---|---|
| 2,718,598 | 9/1955 | Graf | 250/519 |
| 3,602,641 | 8/1971 | Heise | 250/416 TV |
| 3,678,278 | 7/1972 | Pell | 250/445 |
| 3,832,545 | 8/1974 | Bartko | 250/359 |
| 3,883,744 | 5/1975 | Steffel | 250/358 T |

Primary Examiner—Craig E. Church
Attorney, Agent, or Firm—Thomas L. Tully

[57] ABSTRACT

Security inspection apparatus designed for the safe, efficient and rapid inspection of products to detect the presence of objectionable X-ray detectable items. The apparatus comprises a source of continuous X-rays of sufficiently low intensity that conventional photographic film is insensitive thereto, a fluoroscopic screen, a television camera adapted to transmit electrical impulses which provide a visual picture of the images on the fluoroscopic screen to a television monitor and means for intensifying the electrical impulses transmitted by the camera so that the image on the monitor is clearly visible. The apparatus also comprises means for continuously moving products such as baggage between the X-ray source and the screen at a uniform speed within a shielded compartment so that a continuously changing visual picture of the contents of the baggage is displayed on the monitor, providing a three-dimensional picture of each detectable item in the baggage and an indication of its relative location therein.

4 Claims, 6 Drawing Figures

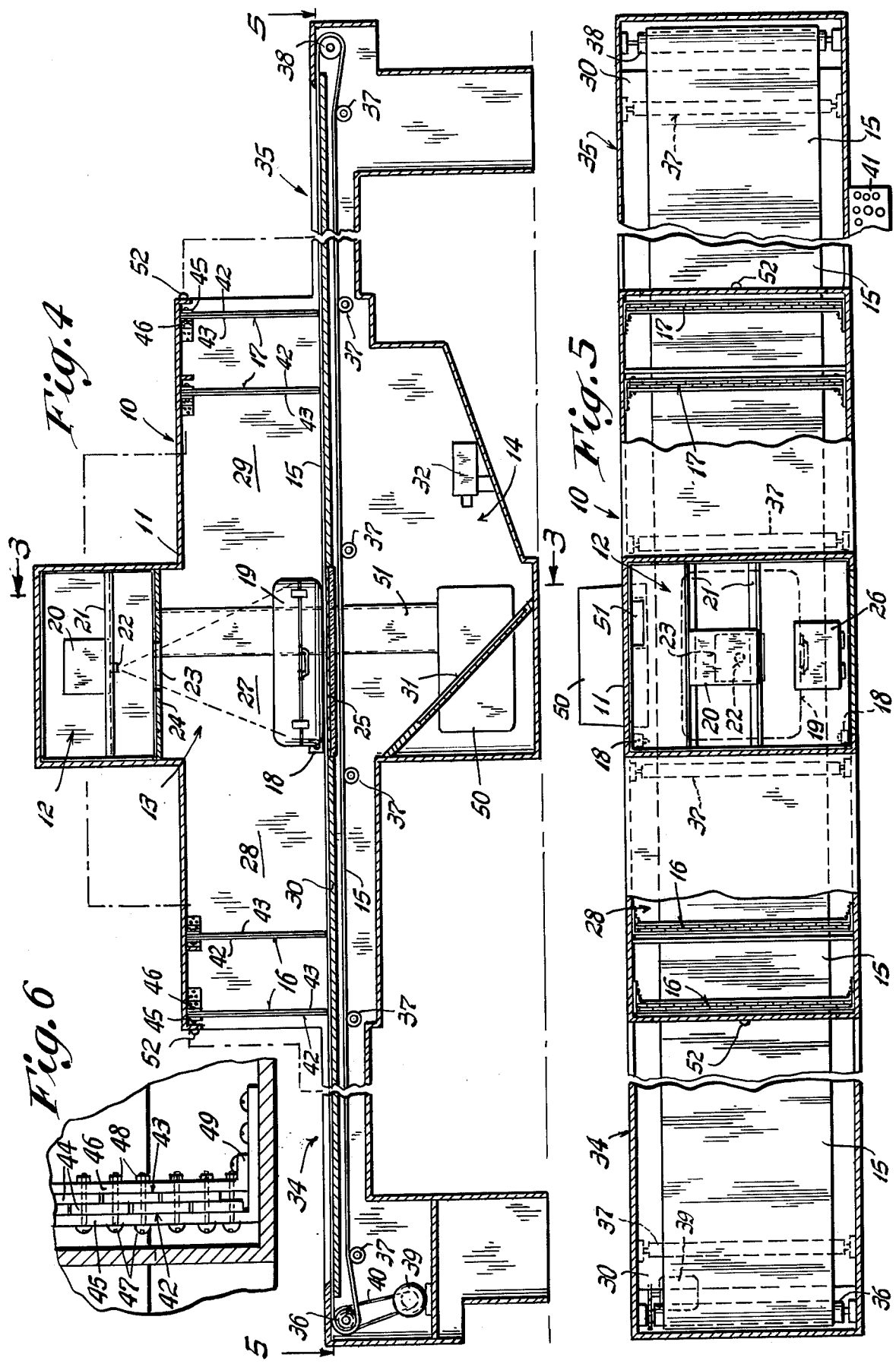

X-RAY INSPECTION DEVICE AND METHOD

This application is a continuation-in-part of parent application Ser. No. 343,566, filed Mar. 21, 1973 now abandoned.

The present invention is primarily concerned with the inspection of carry-on baggage at airports but the present apparatus is also suitable for the inspection of other types of baggage, cargo, prison mail and parcels, logs being conveyed to a cutting blade, and a variety of other X-ray permeable products which may contain X-ray detectable items which are intended to be excluded.

Referring primarily to the inspection of carry-on baggage at airports, it is well known that federal regulations require that all baggage which a passenger carries onto a commercial airplane must first be inspected by ground personnel to insure that bombs, guns or other weapons are not present therein. In order to avoid the delay and embarrassment involved in a personal inspection of such baggage, X-ray inspection devices have been provided which include an X-ray tube, a fluoroscopic screen, a shielded baggage station, and means for viewing the image of the contents of the baggage on the screen either by means of a mirror or as a televised image on a monitor.

There are several disadvantages of known X-ray inspection devices. Firstly, they represent a health hazard unless a substantial amount of expensive lead shielding is used to protect the operator, inspector and passengers. This is due to the fact that X-rays of relatively high and dangerous intensity must be used in order to provide an image on the fluoroscopic screen which is sufficiently visible to the naked eye to permit the rapid and reliable visual detection of wires and other bomb components, thin blades and other small weapons.

Also, conventional photographic film is sensitive to X-rays of such intensity and therefore must be removed from the baggage being inspected or it will be ruined by exposure thereto. This removal is time-consuming, and in many instances the passenger forgets that such film is present in the baggage and valuable film, exposed in a camera, is ruined by exposure to the intense X-rays.

However, the most fundamental disadvantage of known X-ray inspection devices is that they provide a static or fixed picture of the product being inspected. The product is inserted into an inspection station where it lies motionless during exposure to the X-rays and/or the X-ray device is of the "pulse" type whereby a single burst of radiation is released to provide a static picture, even if the product being inspected is in motion. The use of such devices causes delays since the inspection process is not continuous. More importantly, however, a static picture of the contents of a product, such as a piece of luggage, frequently merely provides an indication that the product contains questionable items, requiring the delay and embarrassment of a personal inspection, or a false indication that only permissible items are present. For instance, if a piece of luggage contains several items which are detectable by X-rays, such items may be positioned over each other, either accidentally or intentionally, so that the static picture of the contents shows only the top item, which may be a harmless and permissible item positioned over a hidden weapon, or shows an indiscernible combination of overlapping items, each of which may be harmless and permissible. The inspector may device not to make a personal search in the first case and may decide to make an unnecessary personal search in the second case.

It is the principal object of the present invention to provide a new and improved X-ray inspection device which is faster and more reliable than prior known X-ray inspection devices, obviating the necessity for personal manual inspection in many instances.

It is another object of this invention to provide a novel X-ray inspection device which is safer than prior known X-ray inspection devices from the standpoint of personal exposure to escaping X-rays and exposure of photographic film.

It is still another object of this invention to provide a novel X-ray inspection device which is suitable for the inspection of elongate products and containers, such as logs, storage trunks, flower carbons, and other products which will not fit into the inspection stations of prior known X-ray inspection devices These and other objects and advantages of the present invention will be apparent to those skilled in the art in the light of the present disclosure including the drawing, in which:

FIG. 4 is a cross-sectional front view of the device according to FIG. 1, taken along the line 4—4.

FIG. 5 is a top view of the device according to FIG. 4 taken along the line 5—5.

FIG. 6 is an enlarged segmented top view of a mounting assembly for the shielded curtains of the present device.

The objects and advantages of the present invention are accomplished by the provision of an X-ray inspection device having an X-ray source adapted to continuously emit a divergent beam of X-rays of low intensity, a fluoroscopic screen adapted to receive the X-ray beam, and an inspection station therebetween. Means are provided for continuously moving products to be inspected into and out of the inspection station for exposure to the continuous X-rays, and flexible shielded curtain means cover the entrance and exit of the inspection station to retard the escape of X-rays even when the product being inspected protrudes from either the entrance or the exit during exposure. Also the device is provided with a television camera-viewing monitor system including a signal intensifier whereby the camera views the back surface of the fluoroscopic screen to provide television signals corresponding to the relatively-weak image projected on the screen by the low intensity X-rays, the television signals are intensified and sent to the monitor which projects a visually-clear, sharp and intense picture of the image from the fluoroscopic screen.

Figure 1:
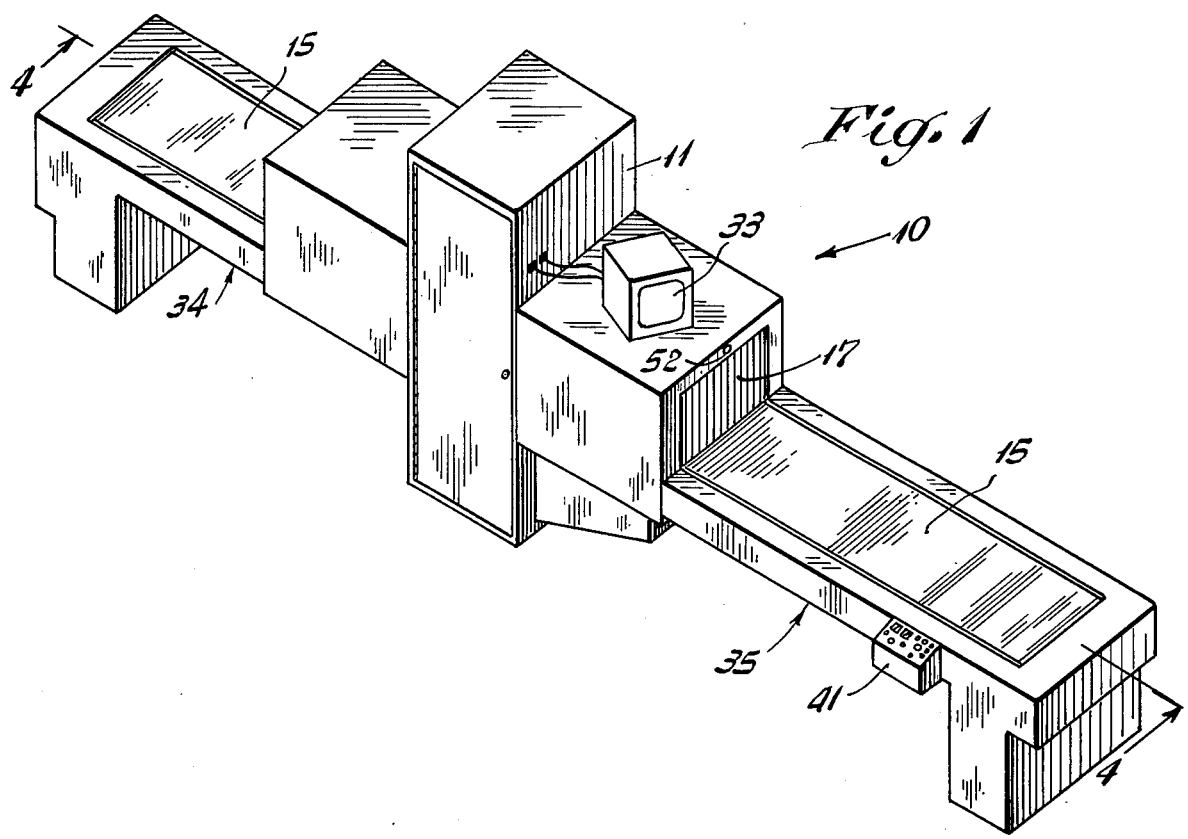
FIG. 1 is a perspective view of an X-ray inspection device according to the present invention.
Figure 2:
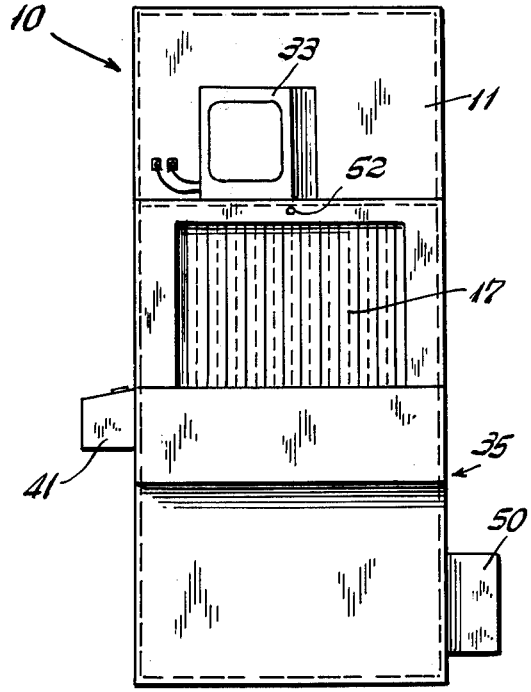
FIG. 2 is an end view of the X-ray inspection device of FIG. 1.

Referring to FIGS. 1 and 4 of the drawings, the present X-ray inspection device 10 comprises a lead-shielded housing 11 having an X-ray tube section 12 and an exposure station 13, and a camera station 14. The exposure station 13 is provided with an automatic conveyor belt 15 which moves products to be inspected into and out of the exposure station at a variable continuous slow speed through spaced banks of flexible shielded entrance curtains 16 and exit curtains 17, as shown in FIG. 4, a photoelectric eye switch 18 being provided at the entrance end of the exposure station 13 to sense the movement of an article 19 into the exposure station 13 and to activate an X-ray emission tube 20 to emit continuous low intensity X-rays for a period of time which extends beyond the time when the article being inspected passes the photoelectric eye beam, i.e. by about 2.5 seconds after the article 19 reaches the location shown in FIG. 4, as regulated by a conventional timing device.

The shielded X-ray tube section 12 comprises an X-ray emission tube 20 mounted on spaced supports 21 so that its radiation collimation orifice 22 is centered with respect to the central opening 23 in the shielded focal member 24. Member 24, such as of lead-shielded plywood, prevents any X-rays from leaving section 12 except through the port or opening 23, and the size of opening 23 and its position relative to the tube 20 and the fluoroscopic screen 25 produces a divergent beam of radiation which strikes only screen 25 and strikes substantially the entire top surface thereof.

Figure 3:
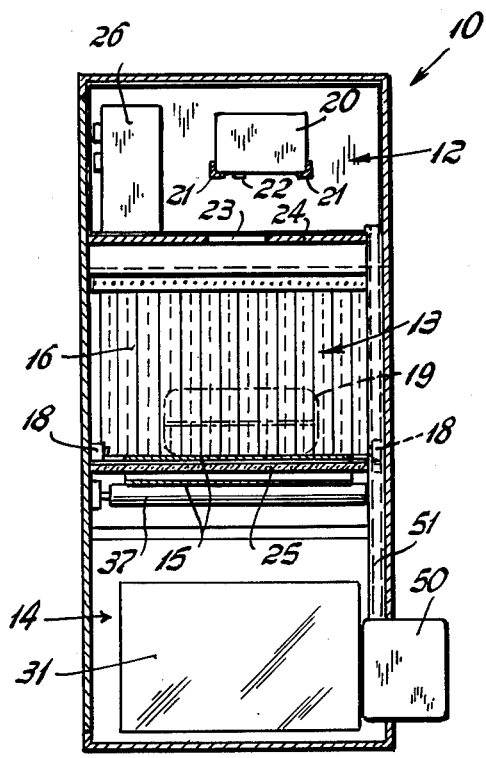
FIG. 3 is an end view of the X-ray inspection device of FIG. 4, taken along the line 3—3.

The X-ray tube section 12 also comprises an X-ray control box 26, shown in FIG. 3, which is associated with the photoelectric eye switch 18 for activating the X-ray tube 20 and includes a timer for deactivating the X-ray tube 20 a predetermined period of time after the photoelectric eye beam is restored by passage of the article being inspected.

The shielded X-ray inspection station 13 comprises a central exposure section 27 and associated entrance section 28 and exit section 29. The photoelectric eye switch 18 is provided at the entrance end of the exposure station 27, as shown in FIGS. 4 and 5. Sections 28 and 29 are provided to accommodate elongate articles being inspected and lead-shielded flexible curtain banks 16 and 17 are provided to permit articles to be conveyed to and from the exposure station 27 while not permitting any of the low intensity X-rays to escape. In most cases the article being inspected, such as luggage article 19, will be completely within the inspection station 13 before the X-ray tube is activated and the latter will be deactivated before the article 19 reaches the interior exit curtain 17. However, even if an elongate article or a succession of smaller articles is conveyed through the shielded inspection station 13, the flexibility of the banks of shielded curtains permits them to conform closely to the surface of the articles, and to close between articles, so that no radiation can escape. Also the low intensity of the radiation and the distance between the exposure station 27 and the outermost curtains 16 and 17 precludes any danger of harmful exposure of the inspector to radiation.

The ceiling of the exposure station 27 comprises the shielded focal member 24 of the X-ray station 12 while the floor of station 27 comprises the fluoroscopic screen 25 which supports the article 19 being conveyed on the belt 15, as shown by FIG. 4. The screen 25 comprises leaded glass to provide a barrier against the passage of the X-rays, whereby the underlying camera station 14 need not be shielded. However the floor or table 30 which is coplanar with the screen 25 and supports the conveyor belt 15 in all areas, except with the exposure station 27, must be shielded insofar as it is located within the entrance section 28 and exit section 29 of the inspection station 13 and between the outermost curtains 16 and 17.

The camera section 14 comprises the shielded fluoroscopic screen 25 as its ceiling, a mirror 31 supported at an angle with respect to the screen 25 and a television camera 32 supported at an angle and distance relative to the mirror whereby the camera 32 can "see" a reflected image corresponding to the entire undersurface of the fluoroscopic screen 25. The mirror 31 permits the camera to be spaced further from the screen 25 so that the entire screen can be exposed to the camera.

The television camera 32 is provided with a special secondary signal booster which increases the sensitivity of the camera and the strength of the signal current transmitted by the camera 32 to the receiver or monitor 33 comprises a cathode ray tube. The present secondary signal booster, more properly called an emission multiplier or photomultiplier tube, provides at least a 1,000 times gain and preferably a 50,000 times gain in signal strength and thus converts the weak, low-intensity X-ray image, which is present on the fluoroscopic screen and is difficult or impossible to discern with the naked eye, into greatly intensified television signals which are transmitted to the monitor to form a sharp, clear, intensified picture on the monitor screen.

The conveyor system for moving articles to be inspected into and out of the inspection station 13 comprises support housings 34 and 35 which support the table 30 and the continuous conveyor belt 15, which moves over the table as it carries articles into and out of the inspection station and returns under the table 30, as shown in FIG. 4. The drive and support mechanism for the continuous belt 15 comprises drive roller 36 in housing 34, spaced idler rollers 37 and support roller 38 rotatably mounted in housing 35. Drive roller 36 is driven by a variable speed motor 39, mounted within support housing 34, in association with a drive belt 40. Motor 39 is electrically connected to control panel 41 and is adapted for normal continuous operation at any desired slow speed. However the control panel includes manual override switch means whereby the speed of the motor may be varied, or the motor may be stopped and reversed by the operator as may be required during the inspection operation.

The ability of the operator or inspector to view the television picture of the fluoroscopic screen 25 on the monitor 33 while the article 19 such as luggage is in motion through the exposure station 27 is an essential feature of the present invention, and the ability to vary the speed of the article, stop its motion and reverse its direction is a preferred embodiment in that it improves the ability of the operator to scrutinize and distinguish the contents of the luggage being inspected. In effect, the operator obtains a three-dimensional view of the contents of the luggage as he views the television monitor 33 which pictures the fluoroscopic screen as the luggage passes thereover from entry position to centered position to exit position. Each detectable item in the luggage produces a continuously changing motion image on the fluoroscopic screen 25 so that its shape and relative position within the piece of luggage are observable on the monitor 33 as the article is conveyed through the X-ray beam. Spaced superposed items can be distinguished as such in a continuous motion exposure whereas a single direct exposure of the same piece of luggage would not show the presence of items shielded beneath other detectable items.

The banks of shielded curtains 16 and 17 form an important part of the present invention since the X-ray tube 20 frequently continues to emit radiation while articles to be inspected are still entering or exiting the inspection station 13. Such is the case when the article being inspected is longer than the distance between the outer curtain 16 or 17 and the center of the exposure station 27, or when a succession of closely-spaced articles are conveyed for inspection. Each of the curtains 16 and 17 and the supports therefor are identical so that the discussion of FIG. 6 of the drawing pertains to each of the four curtains. Thus the curtains comprise contacting superposed layers 42 and 43 of strips 44 of flexible leaded vinyl plastic, each strip being 2 inches wide and abutting against the edge of adjacent strips to provide, in effect, a lead-shielded vinyl plastic film having spaced vertical slits which permit the flexible strips to part and separate under the pressure of an article moved thereagainst. As shown by FIG. 6, the layers 42 and 43 are positioned together so that the vinyl strips 44 of layer 42 overlap the vinyl strips of layer 43 whereby the slits separating the strips of one layer are offset from or out of registration with the slits of the other layer, and any radiation which might escape through the slits of layer 43 will be blocked by a strip 44 of layer 42 which overlies said slit.

As shown by FIG. 6, the upper end of the strips 44 of layers 42 and 43 are sandwiched between 1 inch aluminum bars 45 and 46 which are united by means of a series of bolts 47 and nuts 48 which are spaced by 3 inches so that each bolt passes through one of the strips 44 of each of layers 42 and 43 whereby the strips and layers are held securely in place. Bar 46 is provided with angular end extensions 49 which are bolted to the inside frame of the entrance station 28 and exit section 29 of the inspection station 27.

The novel inspection devices of the present invention are also provided with an air cooling system since the continuous operation of the X-ray tube generates a substantial amount of heat which will build up in the shielded tube section 12 unless air cooling and exhaust means are provided. Thus, a conventional room air conditioner unit 50 is mounted in the frame of the device in the television camera station 14 and an air duct 51 is provided up through the exposure station 13 and through the focal member 24 and opens into the tube station 12. The air conditioner 50 has a fan which circulates the air within the device past refrigerant coils which cool the air. The cool air is then forced by the fan up through the duct 51 into the tube section 12 where it cools the tube 20 and the control box 26. The warm air present in tube section 12 is forced out through the central opening 23 of member 24 into the exposure station 13 where it escapes through curtains 16 and 17 during passage of articles into and out of the inspection station.

Control panel 41 also includes a manual control switch for adjusting the intensity of the X-rays emitted by the X-ray tube in the event that the inspector may find it necessary to activate the X-ray tube with a higher level of X-rays, while articles being inspected are still present in the device, for penetration of denser articles that otherwise might not disclose their contents at the lower level of X-radiation. The lower level of X-rays equals less than 1 millirogentgen/hour and preferably about 0.5 milliroentgen/hour, which levels are harmless to photographic film. The control panel also includes an off-key switch for shutting down the entire device. This switch may be used to deactivate the entire device if the conveyor breaks down or if an article becomes jammed in the station or if the inspector wishes to stop the movement of the article and leave it within the inspection station out of reach by the passenger. Also the device is provided with indicator lights 52 mounted on the outside of the housing above the entrance and exit sections 28 and 29, which lights are associated with the X-ray control box 26 and are illuminated when the X-ray tube is on.

It should be understood that the novel inspection devices of the present invention may be modified in size, shape and design to adapt the device to the inspection of articles of a variety of sizes and shapes, such as products conveyed along an assembly line, logs conveyed into a saw mill, packages conveyed into a prison or consulate, etc.

Variations and modifications may be made within the scope of the claims and portions of the improvements may be used without others.

I claim:
1. Apparatus for the production and visual inspection of the moving fluoroscopic image of an article during movement of said article through said apparatus, comprising a shielded housing, an X-ray exposure station within said housing comprising an X-ray emission station, a fluoroscopic screen shielded against the transmission of X-rays and a baggage inspection station located between said emission station and said screen, said emission station comprising an X-ray emission tube adapted to emit a continuous beam of X-rays of low intensity through said inspection station and onto the surface of said screen, said X-rays being of such low intensity as not to damage photographic film, and a shielded focal member having an opening which focuses all of the X-rays emitted from said emission station as a divergent beams which strikes substantially only the surface of said screen, a television camera adapted to produce video signals corresponding to fluoroscopic images produced on said screen, intensifier means associated with said camera for converting the weak low-intensity X-ray images present on the fluoroscopic screen to video signals which are intensified by a factor of at least about 1000 times gain, a television monitor which is viewable outside said housing by an operator and is associated with said camera and is adapted to receive said intensified video signals and produce intensified television images on said monitor corresponding to the fluoroscopic images present on the fluoroscopic screen, conveyor means for continuously moving an article to be inspected into said X-ray exposure station through an entrance opening in said shielded housing, into said baggage inspection station and out of said shielded housing through another opposed exit opening therein to provide a continuous moving fluoroscopic image of said article passing through said baggage inspection station, sensing means in the area of said entrance opening to sense the entry of an article to be inspected and to activate the X-ray emission tube until a predetermined period of time after the article passes said means, and shielded flexible curtains means covering each of said opposed openings and adapted to retard the escape of X-rays from said inspection station while permitting said article to be conveyed therethrough, said flexible curtain means comprising two spaced banks, each of which comprises two superposed layers of vertically-slit leaded-vinyl plastic, the slits in one of said layers being offset from the slits in the other of said layers.

2. An apparatus according to claim 1 in which said sensing means in the area of said entrance opening comprises photoelectric means.

3. An apparatus according to claim 11 in which said intensifier means is adapted to produce video signals which are intensified by a factor of about 50,000 times gain.

4. An apparatus according to claim 1 in which said conveyor means comprises a continuous conveyor belt driven by a variable speed, reversible motor adapted to vary the speed of and reverse the direction of said belt.

* * * * *